United States Patent [19]

Koichi et al.

[11] Patent Number: 5,464,939
[45] Date of Patent: Nov. 7, 1995

[54] HIGHLY PURIFIED PROTEIN, PRODUCTION AND USE THEREOF

[75] Inventors: Kato Koichi, Kawabe; Yamada Takao, Matsubara; Onda Haruo, Kawanishi, all of Japan

[73] Assignee: Takeda Chemical Industries, Ltd., Osaka, Japan

[21] Appl. No.: 942,358

[22] Filed: Sep. 9, 1992

Related U.S. Application Data

[63] Continuation of Ser. No. 582,778, Sep. 12, 1990, abandoned, which is a continuation of Ser. No. 298,228, Jan. 13, 1989, abandoned, which is a continuation of Ser. No. 674,556, Nov. 26, 1984, abandoned.

[30] Foreign Application Priority Data

Nov. 28, 1983  [JP]  Japan ................... 58-225079

[51] Int. Cl.⁶ ............... C07K 3/00; C12P 21/06; C12N 1/20; C07H 19/00
[52] U.S. Cl. .......... 530/351; 435/69.1; 435/69.5; 435/69.52; 435/252.33; 435/320.1; 530/412; 530/414; 530/416; 530/417; 530/418; 536/22.1; 536/23.1; 536/23.2; 536/23.5
[58] Field of Search ................ 435/69.1, 69.5, 435/69.52, 252.33, 320.1; 530/351, 412, 414, 416, 417, 418; 536/22.1, 23.1, 23.2, 23.5

[56] References Cited

U.S. PATENT DOCUMENTS

| | | |
|---|---|---|
| 4,490,289 | 12/1984 | Stern . |
| 4,518,584 | 5/1985 | Mark et al. . |
| 4,530,787 | 7/1985 | Shaked et al. . |
| 4,564,593 | 1/1986 | Tsukamoto et al. ............ 530/351 |
| 4,569,790 | 2/1986 | Koths et al. . |

FOREIGN PATENT DOCUMENTS

| | | |
|---|---|---|
| 0089692 | 3/1983 | European Pat. Off. . |
| 0091539 | 3/1983 | European Pat. Off. . |
| 0092163 | 4/1983 | European Pat. Off. . |
| 89062A2 | 8/1983 | European Pat. Off. . |
| 094317 | 11/1983 | European Pat. Off. . |
| 0118617 | 12/1983 | European Pat. Off. . |
| 0119621A1 | 9/1984 | European Pat. Off. . |
| 0118977A1 | 9/1984 | European Pat. Off. . |
| 118977A1 | 9/1984 | European Pat. Off. . |
| WO85/02200 | 5/1985 | WIPO . |

OTHER PUBLICATIONS

Riendeau, D., et al., Journal of Biological Chemistry 258(20):12114–12117 (1983).

1062 TMOG 137, Jan. 7, 1986.

Fred E. Regnier et al., "High–Performance Liquid Chromatography of Proteins", Analytical Biochemistry 103, 1–25 (1980).

Hans Neurath et al., "The Proteins", p. 198, 1975.

James W. Mier et al., "Purification and some characteristics of human T-cell growth factor from phytohemagglutinin–stimulated lymphocyte–conditioned media", Proc. Natl. Acad. Sci. USA vol. 77, No. 10 pp. 6134–6138, Oct. 1980.

Harald S. Conradt et al., "Structures of the major carbohydrates of natural human interleukin–2", Eur. J. Biochem. 153, 255–261 (1985).

(List continued on next page.)

Primary Examiner—Robert Wax
Assistant Examiner—Hyosuk Kim
Attorney, Agent, or Firm—David G. Conlin; Ronald I. Eisenstein

[57] ABSTRACT

A substantially pure non-glycosylated human interleukin-2 protein having a specific activity of not less than $10^4$ U/mg is obtained by growing a transformant carrying a DNA having a base sequence coding for human interleukin-2 to cause production and accumulation of human interleukin-2 in the culture broth, subjecting the thus obtained human interleukin-2-containing liquid to a purification process comprising a hydrophobic column chromatography.

15 Claims, 8 Drawing Sheets

OTHER PUBLICATIONS

Steven Gillis et al., "Biochemical Characterization of Lymphocyte Regulatory Molecules", The Journal of Immunology vol. 124, No. 4, Apr. 1980.

Programme and Abstracts, 3rd International Symposium on HPLC of Proteins, Peptides and Polynucleotides, Nov. 14–16, 1983.

Louis E. Henderson et al. "A Rapid, Large Scale Purification For Gibbon Interleukin 2[1]", The Journal of Immunology, vol. 131, No. 2, Aug., 1983.

J. Immun. 133 (2) 1078 (Aug. 1984).

"Biological Response Modifiers Program (Ad)", J. Immun. 133 (Aug. 1984).

Biochem & Biophysical Res. Comm. 135 (3):837–843 (1986).

Biochem & Biophysical Res. Comm. 130 (2):692–699 (1985).

Biochem. & Biophysical Res. Comm. 128 (1):257–264 (1985).

Biochem. & Biophysical Res. Comm. 127 (1):182–190 (1985).

Science, 193, 1007–1008 (1976).

Immunological Reviews, 51, 257–278 (1980).

The Journal of Immunology, 123, 2928–2929 (1979).

Nature, 268, 154–156 (1977).

The Journal of Immunology, 130, 981–987 (1983).

The Journal of Immunology, 125, 1904–1909 (1980).

The Journal of Immunology, 130, 1784–1789 (1983).

The Journal of Immunology, 130, 1970–1973 (1983).

European Journal of Immunology, 10, 719–722 (1980).

Nature, 284, 278–280 (1980).

Nature, 302, 305–310 (1983).

Nucleic Acids Research, 11, 4307–4323 (1983).

Biochemical and Biophysical Research Communication, 109, 363–369 (1982).

Cell, 8, 163–182 (1976).

Nucleic Acids Research 9, 2251–2266 (1981).

Methods in Enzymology, 68, 41–50 (1979).

Proc. Natl. Acad. Sci. USA, 72, 3961–3965 (1975).

Method in Enzymology, 68, 220–242 (1979).

Proc. Natl. Acad. Sci. USA, 74, 560–564 (1977).

Nucleic Acids Research, 9, 309–321 (1981).

Proc. Natl. Acad. Sci. USA, 73, 4174–4178 (1976).

Nature, 217, 1110–1114 (1968).

Cell, 25, 713–719 (1981).

Proc. Natl. Acad. Sci. USA, 69, 2110–2114 (1972).

J. Experiments in Molecular Genetics, pp. 431–433 (Cold spring Harbor Laboratory, New York, 1972).

Journal of Immunology, 130, 988–992 (1983).

The Journal of Immunology, 120, 2027–2032 (1978).

Haemostasis, 7, 183–188 (1978).

J. Molecular Biology, 96, 495–509 (1975).

Proc. Natl. Acad. Sci. USA, 75, 5765–5769 (1978).

Nucleic Acids Research, 9, 6103–6114 (1981).

Nucleic Acids Research, 7, 1513–1523 (1979).

Methods in Enzymology, 11, 197–199 (1967).

Analytical Biochem., 67, 438–445 (1975).

Nucleic Acids Research, 11, 3077–3085 (1983).

Nucleic Acids Research, 11, 4307–4323 (1983).

J. Exp. Med., 156, 454–464 (1982).

Proc. Natl. Acad. Sci. USA, 80, 5990–5994 (1983).

```
5'GGGGGGGGGGGGGGGGGGATCACTCTCTTTAATCACTACTCACAGTAACC

S1
TCAACTCCTGCCACA ATG TAC AGG ATG CAA CTC CTG TCT TGC

S20  1
ATT GCA CTA AGT CTT GCA CTT GTC ACA AAC AGT GCA CCT

ACT TCA AGT TCT ACA AAG AAA ACA CAG CTA CAA CTG GAG

20
CAT TTA CTG CTG GAT TTA CAG ATG ATT TTG AAT GGA ATT

40
AAT AAT TAC AAG AAT CCC AAA CTC ACC AGG ATG CTC ACA

TTT AAG TTT TAC ATG CCC AAG AAG GCC ACA GAA CTG AAA

60
CAT CTT CAG TGT CTA GAA GAA GAA CTC AAA CCT CTG GAG

80
GAA GTG CTA AAT TTA GCT CAA AGC AAA AAC TTT CAC TTA

AGA CCC AGG GAC TTA ATC AGC AAT ATC AAC GTA ATA GTT

100
CTG GAA CTA AAG GGA TCT GAA ACA ACA TTC ATG TGT GAA

TAT GCT GAT GAG ACA GCA ACC ATT GTA GAA TTT CTG AAC

120
AGA  TGG ATT ACC TTT TGT CAA AGC ATC ATC TCA ACA CTG

133
ACT TGA TAATTAAGTGCTTCCCACTTAAAACATATCAGGCCTTCTATTT

ATTTAAATATTTAAATTTTACCCCCCCCCCCCCCC3'
```

FIG. 2

```
   1
X-Ala Pro Thr Ser Ser Ser Thr Lys Lys Thr Gln Leu Gln

20
Leu Glu His Leu Leu Leu Asp Leu Gln Met Ile Leu Asn

Gly Ile Asn Asn Tyr Lys Asn Pro Lys Leu Thr Arg Met

40
Leu Thr Phe Lys Phe Tyr Met Pro Lys Lys Ala Thr Glu

60
Leu Lys His Leu Gln Cys Leu Glu Glu Glu Leu Lys Pro

Leu Glu Glu Val Leu Asn Leu Ala Gln Ser Lys Asn Phe

80
His Leu Arg Pro Arg Asp Leu Ile Ser Asn Ile Asn Val

100
Ile Val Leu Glu Leu Lys Gly Ser Glu Thr Thr Phe Met

Cys Glu Tyr Ala Asp Glu Thr Ala Thr Ile Val Glu Phe

120
Leu Asn Arg Trp Ile Thr Phe Cys Gln Ser Ile Ile Ser

133
Thr Leu Thr
```

FIG. 3

HIGHLY PURIFIED PROTEIN, PRODUCTION AND USE THEREOF

This is a continuation of application(s) Ser. No. 07/582,778 filed on Sep. 12, 1990, now abandoned, which is a continuation of Ser. No. 07/298,228 filed on Jan. 13, 1989, now abandoned, which is a continuation of Ser. No. 06/674,556, filed on Nov. 26, 1984, now abandoned.

This invention relates to a human interleukin-2 protein and a method of producing the same by a genetic engineering technique.

Interleukin-2 [also called T cell growth factor (TCGF); hereinafter abbreviated as IL-2] is a lymphokine produced by T cells upon stimulation with a lectin or alloantigen, for example [Science, 193, 1007 (1976); Immunological Reviews, 51, 257 (1980)]. IL-2 facilitates long-period culture of T cells by enabling said cells grow in vitro while retaining their biological functions. Furthermore, IL-2 reportedly promotes the mitogen reaction of thymus cells (costimulator), restores the production by spleen cells of antibodies against T cell-dependent antigens in nude mice (T cell replacing factor) and/or promotes the differentiation and proliferation of killer cells (killer helper factor) [The Journal of Immunology, 123, 2928 (1979); Immunological Reviews, 51, 257 (1980)].

Killer T cell clones, helper T cell clones and, further, natural killer cell clones have been cloned through the utilization of IL-2 [e.g., Nature, 268, 154 (1977); The Journal of Immunology, 130, 981 (1983)]. In addition to such direct use in T cell or natural killer cell cloning, IL-2 can be used in selectively growing killer T cells specific for certain antigens, for example killer T cells recognizing a tumor antigen and thereby destroying the tumor, in vitro. By injecting the tumor-specific killer T cells produced by use of IL-2 into an animal, it is possible to inhibit and prevent the tumor growth [The Journal of Immunology, 125, 1904 (1980)]. It is also known that IL-2 induces the production of IFN-γ [The Journal of Immunology, 130, 1784 (1983)] and that IL-2 activates natural killer cells [The Journal of Immunology, 130, 1970 (1983)].

The above experimental data suggest that IL-2 is useful as an antitumor agent. IL-2 is known to restore the helper T cell function in nude mice lacking thymic function [European Journal of Immunology, 10, 719 (1980)] or restore the induction of killer T cells against homologous cells [Nature, 284, 278 (1980)] and, therefore IL-2 is useful in treating immunocompromised diseases.

Large scale production of IL-2 by methods known in the art has been unsuccessful. The development of clinical applications thereof has therefore been hindered by the scarcity and purity of IL-2. Accordingly, a technique for the production of highly purified IL-2 in large amounts, in an easy and simple manner and at low cost is highly desirable.

Taniguchi et al. cloned a human IL-2 gene by using IL-2 mRNA isolated from the human T cell leukemia line Jurkat as the starting material, reported the amino acid sequence of human IL-2 protein as deduced therefrom and expressed the gene in COS-7 cells [Nature, 302, 305 (1983)]. Later, Devos et al. reported that a human spleen cell-derived IL-2 gene had been cloned and expressed in *Escherichia coli* [Nucleic Acids Research. 11, 4307 (1983)]. Nevertheless, so far, the presence of an IL-2-like substance has only been estimated on the basis of detectable TCGF activity and there has been no report that a human IL-2 protein produced by a transformant carrying a DNA coding for human IL-2 has been isolated in a purified form.

The present inventors have developed a technique by which substantially pure non-glycosylated IL-2 protein can be obtained through cloning a human IL-2 gene utilizing the gene manipulation technology, introduction of the recombinant DNA molecule obtained thereby into a host and expression of the human IL-2 gene in said host, and as a result could establish a method of producing a substantially pure, non-glycosylated human IL-2 protein and have completed the present invention.

Thus, the present invention provides a substantially pure, non-glycosylated human IL-2 protein and a method of producing said human IL-2 protein which comprises cultivating a transformant carrying a DNA having a base sequence coding for human IL-2 and purifying said protein from the culture broth.

DNA coding for human IL-2 to be used in the practice of the present invention is, for example, a DNA (I) having the base sequence defined by codons 1–133 in FIG. 2. This DNA (I), may have, at its 5' end, either ATG or a signal sequence represented in FIG. 2 by codons S1–S20 and, at its 3' end, preferably has TAA, TGA or TAG, more preferably TGA.

The DNA (I) is preferably connected downstream from a promoter, for example the tryptophan (trp) promoter, rec A promoter or λPL promoter, more preferably the trp or λPL promoter.

In accordance with the invention; the mRNA coding for human IL-2 is isolated from a culture of human peripheral leukocytes stimulated by concanavalin A, for instance, then a single-stranded cDNA is synthesized therefrom using reverse transcriptase, and further a double-stranded DNA is synthesized. Double-stranded DNA is inserted into a plasmid, the recombinant plasmid is used for transformation of a strain of *Escherichia coli* or *Bacillus subtilis,* for example, and the cDNA-containing plasmid is cloned. In this way, a double-stranded DNA coding for human IL-2 can be produced.

More particularly, a human IL-2-encoding mRNA to be used in the practice of the invention can be obtained by the method of Hinuma et al. [Biochemical and Biophysical Research Communications, 109, 363 (1982)]. With the thus-obtained human IL-2 mRNA as a template, a cDNA is synthesized by the per se known method using reverse transcriptase, and the cDNA is converted to a double-stranded DNA [Maniatis, T. et al. Cell, 8, 163 (1976); Land, H. et al., Nucleic Acids Research, 9, 2251 (1981)]. The double-stranded DNA is inserted, for example, into the plasmid pBR322,at the PstI restriction endonuclease cleavage site by the dG-dC homopolymer ligation method [Nelson, T. S., Methods in Enzymology, 68, 41 (1979)], for instance. Furthermore, an oligonucleotide having a base sequence corresponding to the amino acid sequence of a part of human IL-2, for instance, is chemically synthesized and then labeled with $^{32}P$. Using this as a probe, a desired clone is selected from among tetracycline- or ampicillin-resistant transformants by the per se known colony hybridization method [Grunstein, M. and Hogness, D. S., Proc. Natl. Acad. Sci. USA, 72, 3961 (1975); Alwine, J. C. et al., Methods in Enzymology, 68, 220 (1979)]. The presence of a human IL-2 gene is confirmed by determination of the base sequence of DNA derived from a clone selected by means of the above hybridization method by Maxam-Gilbert method [Maxam, A. M. et al., Proc. Natl. Acad. Sci. USA, 74, 560 (1977)] or the dinucleotide synthetic chain termination method using phage M13 [Messing, J. et al., Nucleic Acids Research, 9, 309 (1981)]. Then, a complete or partial human IL-2 gene is excised from a selected clone obtained and inserted into a plasmid downstream from an appropriate promoter and the SD (Shine and Dalgarno) base sequence, for the subsequent introduction into an appropriate host.

The use of the trp promoter, among others, as the promoter is preferred. As the host, a strain of *Escherichia coli* (e.g. strain 294, strain DH1, strain N4830), among others, is preferred.

The strains *Escherichia coli* 294 [Beckman et al., Proc. Natl. Acad. Sci. USA, 73, 4174 (1976)], *E. coli* DH1 [Selson, M. E. et al., Nature, 217, 1110 (1968)] and *E. coli* N4830 [Cell, 25, 713 (1981) ] are known available strains.

The transformation of such hosts with the DNA is performed by the known method [Cohen, S. N. et al., Proc. Natl. Acad. Sci. USA, 69, 2110 (1972)]. A transformed host thus obtained is cultivated in a per se known medium, such as glucose- and casamino acid-containing M9 medium [Miller, J. Experiments in Molecular Genetics, pages 431–433 (Cold Spring Harbor Laboratory, New York, 1972)]. In cases where the trp promoter is used, an agent such as 3-β-indolylacrylic acid may be added for increasing the efficiency of said promoter. The cultivation is generally carried out at 15°–43° C. for 10–30 hours, preferably 18–24 hours, with aeration and/or stirring as necessary.

In a case where the λPL promoter is used, the cultivation is preferably carried out at a relatively low temperature of about 30° to 36° C. to grow the transformants and then of about 37° to 42° C. to inactivate the repressor in the transformants and to effectively express the DNA coding for human IL-2.

Human IL-2 thus formed may be assayed using an IL-2-dependent cell line. Since human IL-2 is known to promote the growth of rat, mouse or other IL-2-dependent cells as well as human IL-2-dependent cells [Immunological Reviews, 51, 257 (1980)], not only IL-2-dependent human cell lines but also rat or mouse IL-2-dependent cell lines may be used for the assay [Journal of Immunology, 130, 981 and 988 (1983)]. The thus obtained IL-2 can be used to maintain desired cell lines which are IL-2 dependent.

In particular, mouse IL-2-dependent cell lines may be maintained stably by subculturing for a long period of time, so that their use can give highly reproducible assay results.

In extracting human IL-2 according to the invention from cultivated cells, the cells, after cultivation, are harvested by known methods, suspended either in a solution of a protein denaturing agent such as a mineral acid salt of guanidine (e.g. hydrochloride, nitrate, sulfate), and the suspension is stirred in the cold and then centrifuged, whereby an IL-2-containing supernatant is obtained, or in a buffer and disrupted by sonication, lysozyme treatment and/or freezing and thawing, followed by centrifugation to give an IL-2-containing supernatant. Any other method which is useful to extract IL-2 may also be used.

The isolation of IL-2 from the above supernatant and the subsequent purification of the same can be carried out by an appropriate combination of per se known methods of separation and purification. Such known separation and purification methods include, among others, methods utilizing solubility differences such as salting out methods and solvent precipitation methods, methods utilizing molecular weight differences in the main, such as dialysis, ultrafiltration, gel filtration and SDS-polyacrylamide gel electrophoresis, methods utilizing charge differences, such as ion exchange chromatography, methods utilizing specific affinities such as affinity chromatography, methods utilizing hydrophobicity differences, such as reversed phase high performance liquid chromatography, and methods utilizing isoelectric point differences, such as isoelectric focusing. Since human IL-2 protein is highly hydrophobic, hydrophobic column chromatography, in particular high performance liquid chromatography using a reversed phase column, is preferred in purifying said protein.

Thus, for example, the cells obtained by cultivating a strain of *Escherichia coli* carrying a gene coding for human IL-2 are suspended in a solution, preferably in a buffer of a protein denaturing agent such as guanidine hydrochloride(in a concentration of 2M to 8M, preferably 6M–8M), and the suspension is stirred, preferably at 0°–5° C. for 0.5–3 hours and then centrifuged. The supernatant thus collected is, if appropriate, concentrated using an ultrafiltration device or the like and subjected to dialysis. The resulting precipitate, if any, is removed by centrifugation and the supernatant is subjected to anion exchange chromatography using diethylaminoethylcellulose [e.g. DE 52 cellulose (Whatman, Gt. Britain) column], for example, and an active, i.e. having IL-2 activity, fraction is collected.

Then, after concentration using an ultrafiltration device, the active fraction is subjected to gel filtration using N,N'-methylenebisacrylamide-crosslinked allyldextran, such as a Sephacryl S-200 (Pharmacia, Sweden) column, or the like. The active fraction collected is then subjected to the abovementioned high performance liquid chromatography. In this manner, non-glycosylated human IL-2 according to the invention can be obtained.

As the reversed phase system to be used in high Performance liquid chromatography, resin coated with alkylated ($C_{1-18}$) silanes are effectively used among others. As the eluent, a $C_{1-6}$ lower alkanol (e.g. ethanol, propanol) or acetonitrile can advantageously be used and the eluent has a pH of 1.5–8, preferably 1.5–4. The rate of elution is 0.1–100 ml/min, preferably 0.5–10 ml/min.

Human IL-2 protein thus obtained can be turned into a powder by lyophilization as necessary. On the occasion of lyophilization, a stabilizer such as sorbitol, mannitol, dextrose, maltose, glycerol or human serum albumin (HSA) may be added.

When assayed for IL-2 activity using, as the index, the radioactive thymidine uptake by IL-2-dependent mouse cells, human IL-2 protein obtained in accordance with the present invention shows a specific activity of not less than $1 \times 10^4$ U/mg. In accordance with the invention, there can be obtained a highly pure, non-glycosylated human IL-2 protein having a specific activity of not less than $10^4$ U/mg, and preferably about $2 \times 10^4$ U/mg to $4 \times 10^4$ U/mg.

As mentioned herein, the IL-2 activity in units (U) may be calculated in the following manner.

Thus, an IL-2-containing sample is added to a medium containing cells of a mouse cell line which grow depending on the concentration of IL-2, and the whole mixture is incubated at 37° C. overnight in the presence of 5% $CO_2$, the growth of said-cell line may be determined using tritiated thymidine. For calculating the IL-2 activity in units (U) in the sample in question, a standard IL-2 (1 U/ml) is used for comparison and said activity in units is calculated from the activity ratio between the sample and the standard.

More particularly, cells of an IL-2-dependent mouse cell line (NKC3) [Hinuma et al., Biochem. Biophys. Res. Commun., 109, 363 (1982)] maintained by subculturing in 20% FCS-added RPMI 1640 medium supplemented with an IL-2-containing conditioned medium at 37° C. in the presence of 5% $CO_2$ are washed twice with a serum-free RPMI 1640 medium and resuspended in 20% FCS-added RPMI 1640 medium to $6 \times 10^5$ cells/ml.

An IL-2-containing sample is distributed, in 50-μl portions, into the wells in the first row of a 96-well flat-bottomed microtiter plate (Nunc, Denmark). Using 50-μl portions of 20% FCS-added RPMI 1640 medium, a two fold serial dilution is produced until the 12th row. Then the above-mentioned NKC3 cell suspension is distributed, in 50-μl portions, into all the wells, followed by incubation at 37° C. in the presence of 5% $CO_2$ for 24 hours. After 20 hours of incubation, 1 μCi of tritiated thymidine (Amersham, Great Britain) is added to each well. After continued incubation for 4 hours, cells are recovered onto a glass filter using a cell harvester (Flow, USA) and measured for tritiated thymidine uptake using a liquid scintillation counter. In carrying out the above assay, a standard IL-2 sample is subjected to the same procedures as an IL-2 containing sample to be assayed and the tritiated thymidine uptake is determined.

The calculation of the activity in units (U) is carried out by the probit method according to the Journal of Immunology, 120, 2027 (1978). Thus, the maximum uptake in the standard IL-2 sample dilution series is regarded as 100%, and the percentage (%) of the uptake for each dilution stage is calculated. The values thus obtained are plotted on a normal probability paper and the dilution factor at which the uptake is 50% is determined graphically. Also for each IL-2-containing sample, the dilution factor at which the uptake is 50% is determined in the same manner. The amount of IL-2 activity contained in the culture supernatant after 48 hours of incubation, at 37° C. in the presence of 5% $CO_2$, of a suspension of human peripheral blood lymphocytes ($5 \times 10^6$ cells/ml) in 10% FCS-added RPMI 1640 medium supplemented with 40 μg/ml of concanavalin A and 15 ng/ml of 12-O-tetradecanoylphorbol- 13-acetate is defined as 1 U/ml.

The IL-2 concentration (U/ml) of the sample is calculated by the formula:

$$\frac{\text{Dilution factor for sample at which 50\% uptake is attained}}{\text{Dilution factor for standard IL-2 sample at which 50\% uptake is attained}}$$

The natural IL-2 obtained from the human peripheral blood had a specific activity of 20,000–70,000 U/mg as determined by the above assay method. This activity is almost equal to the activity of non-glycosylated human IL-2 protein according to the present invention.

Non-glycosylated human IL-2 protein according to the invention preferably comprises the polypeptide (II) having the amino acid sequence shown in FIG. 3 wherein X is Met or hydrogen.

Human IL-2 protein produced in accordance with the invention has the following characteristics:

1) It is homogeneous in SDS-polyacrylamide gel electrophoresis and has a molecular weight of 15,000±1,000 daltons as determined by said electrophoresis;

2) It contains alanine or methionine as the amino-terminal amino acid;

3) It contains threonine as the carboxy-terminal amino acid;

4) It promotes growth of T cells or natural killer cells while maintaining their functions.

Human IL-2 protein produced in accordance with the invention reacts negatively in the limulus lysate test [Haemostasis, 7, 183 (1978)] and is low in protein impurities and pyrogen content, so that it can be used safely as a bulk substance for manufacturing injections and so on.

Non-glycosylated human IL-2 protein obtained in accordance with the present invention has an activity of promoting the growth of normal T cells or natural killer cells while maintaining their functions. Therefore, IL-2 protein according to the invention can be used in growing and subculturing T cells or natural killer cells in vitro for a long period of time or cloning the same. Moreover, this property can be utilized in human IL-2 activity measurement.

Furthermore, human IL-2 protein of the invention makes it possible to selectively grow antigen-specific killer T cells, which recognize and destroy tumor antigens, or natural killer cells, which are capable of killing tumor cells irrespective of the presence or absence of an experience of antigenic sensitization, in vitro. When inoculated into a living organism simultaneously with the introduction of said killer cells into the living organism, human IL-2 of the present invention increases the anti-tumor effete of killer T cells. Therefore, said IL-2 is useful for the prevention or treatment of tumors or the treatment of immunodeficiency diseases in warm-blooded mammals (e.g. mouse, rat, rabbit, dog, cat, pig, horse, sheep, cattle, human).

Human IL-2 protein according to the present invention is a highly purified product and has little antigenicity for humans and is low in toxicity.

As an agent for the prevention and treatment of tumors, human IL-2 protein of the invention can be administered either parenterally or orally in the form of, for example, injections or capsules prepared by appropriate blending or dilution with a per se known carrier. It can be used either alone or in combination with killer T cells or natural killer cells grown in vitro, as mentioned hereinbefore.

Human IL-2 protein according to the present invention has substantially the same biological activity as the natural human IL-2 and accordingly can be used in the same manner as said natural IL-2. The dissociation constant of IL-2 in relation to the IL-2 receptor of the responding cells is very small, so that a very small dose is sufficient in most cases.

For the purpose of growing T cells in vitro, the human IL-2 of the invention can be added to the medium in a concentration of about 0.01–1 U/ml, preferably about 0.1–0.5 U/ml.

In an example of the use for the purpose of growing T cells in vitro, IL-2 protein of the invention is added, at a concentration of 0.1–0.5 unit/ml, to a cell suspension containing, for example, alloantigen-sensitized T cells obtained by 3-day mixed lymphocyte culture of human peripheral blood-derived T cells ($1 \times 10^6$ cells/ml), with B cell transformants ($1 \times 10^6$ cells/ml) resulting from X ray irradiation (1,500 rads) added, in RPMI 1640 medium containing 20% of fetal bovine serum. Cultivation is continued for about 1 month while repeating medium exchange an about one-week intervals.

The transformant disclosed in the following examples, namely *Escherichia coli* DH1/pTF4, has been deposited at Institute for Fermentation, Osaka (IFO) under the deposit number IFO-14299, and also deposited at Fermentation Research Institute, Agency of Industrial Science and Technology, Ministry of International Trade and Industry, Japan (FRI) under the accession number of FERM BP-628 of a deposit under the Budapest Treaty.

In the present specification and drawings, the bases and amino acids, when indicated by abbreviations, are abbreviated according to the rules of the IUPAC-IUB Commission on Biochemical Nomenclature or the practice in the field concerned. Examples are shown in Table 1. Where optical isomerism is involved, the amino acids mentioned are in the L form unless otherwise specifically indicated.

TABLE 1

| | |
|---|---|
| DNA: | Deoxyribonucleic acid |
| CDNA: | Complementary deoxyribonucleic acid |

TABLE 1-continued

| | |
|---|---|
| A: | Adenine |
| T: | Thymine |
| G: | Guanine |
| C: | Cytosine |
| RNA: | Ribonucleic acid |
| mRNA: | Messenger ribonucleic acid |
| DATP: | Deoxyadenosine triphosphate |
| DTTP: | Deoxythymidine triphosphate |
| dGTP: | Deoxyguanosine triphosphate |
| dCTP: | Deoxycytidine triphosphate |
| ATP: | Adenosine triphosphate |
| EDTA: | Ethylenediaminetetraacetic acid |
| SDS: | Sodium dodecyl sulfate |
| Gly: | Glycine |
| Ala: | Alanine |
| Val: | Valine |
| Leu: | Leucine |
| Ile: | Isoleucine |
| Ser: | Serine |
| Thr: | Threonine |
| Cys: | Cysterine |
| ½ Cys: | Half cystine |
| Met: | Methionine |
| Glu: | Glutamic acid |
| Asp: | Aspartic acid |
| Lys: | Lysine |
| Arg: | Arginine |
| His: | Histidine |
| Phe: | Phenylalanine |
| Tyr: | Tyrosine |
| Trp: | Tryptophan |
| Pro: | Proline |
| Asn: | Asparagine |
| Gln: | Glutamine |

BRIEF DESCRIPTION OF THE DRAWINGS

FIG. 1 and FIG. 2 show the restriction enzyme map of the plasmid pILOT135-8 obtained in Reference Example 1 (vii) (▧▧▧indicating the portion coding for the signal peptide and ▨▨▨indicating the portion coding for IL-2) and the primary structure (base sequence) of said plasmid, respectively. FIG. 3 shows the amino acid sequence of the non-glycosylated human IL-2 protein according to the invention, wherein X is Met or a hydrogen atom.

REFERENCE EXAMPLE 1

Figure 1:
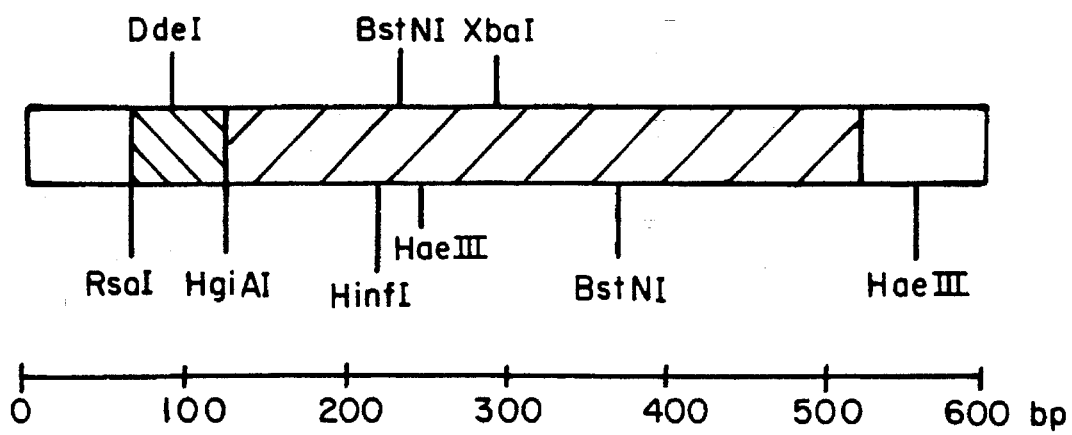

(i) Isolation of mRNA coding for human IL-2

Lymphocytes prepared from human peripheral blood were incubated in RPMI 1640 medium supplemented with 10% fetal bovine serum, 12-O-tetradecanoylphorbol-13-acetate (TPA) (15 ng/nl) and concanavalin A (40 µg/ml) at 37° C. to thereby induce production of IL-2. After 24 hours of incubation, 1×10¹⁰ human lymphocytes thus induced were disrupted and denatured in a solution containing 5M guanidine thiocyanate, 5% mercaptoethanol, 50 mM Tris·HCl (pH 7.6) and 10 mM EDTA using a Teflon homogenizer, then sodium N-lauroylsarcosinate was added to a concentration of 4%, and the mixture, after homogenization, was layered onto 6 ml of 5.7M cesium chloride solution (5.7M cesium chloride, 1M EDTA) and centrifuged using a Beckman SW28 rotor at 24,000 rpm and 15° C. for 48 hours, to give an RNA precipitate. This RNA precipitate was dissolved in 0.25% sodium N-lauroylsarcosinate and precipitated with ethanol to give 10 mg of RNA. In a high-concentration salt solution (0.5 M NaCl, 10 mM Tris·HCl pH 7.6, 1 mM EDTA, 0.3% SDS), this RNA was adsorbed on an oligo(dT-)cellulose column. Elution with a low-concentration salt solution (10 mM Tris·HCl pH 7.6, 1 mM EDTA, 0.3% SDS) gave 300 µg of poly(A)-containing mRNA. This mRNA was further subjected to precipitation with ethanol, then dissolved in 0.2 ml of a solution (10 mM Tris·HCl pH 7.6, 2mM EDTA, 0.3% SDS), treated at 65° C. for 2 minutes and fractionated by 10–35% sucrose density gradient centrifugation (at 20° C. and 25,000 rpm for 21 hours using a Beckman SW28 rotor) into 22 fractions. An aliquot of each fraction was injected into oocytes of *Xenopus laevis* and the IL-2 activity in proteins thus synthesized was measured. Fractions Nos. 11–15 (sedimentation coefficient 8S–15S) were found to have IL-2 activity. About 25 µg of IL-2 mRNA was contained in these fractions.

(ii) Synthesis of single-stranded DNA

Using the mRNA obtained above and reverse transcriptase, synthesis of single stranded cDNA was carried out in 100 µl of reaction solution (5 µg of mRNA, 50 µg of oligo(dT), 100 units of reverse transcriptase, 1 mM dATP, 1 mM dCTP, 1 mM dGTP, 1 mM dTTP, 8 mM MgCl₂, 50 mM KCl, 10 mM dithiothreitol, 50 mM Tris·HCl pH 8.3) at 42° C. for 1 hour, followed by deproteinization with phenol and treatment with 0.1N NaOH at 70° C. for 20 minutes for removal of RNA by decomposition.

(iii) Synthesis of double-stranded DNA

Double-stranded DNA encoding IL-2 was synthesized by treating the thus-synthesized single-stranded complementary DNA obtained in (ii) above in 50 µl of a reaction solution (the same as the above-mentioned reaction solution of step (ii) except that mRNA and oligo(dT) were absent) at 42° C. for 2 hours. See Maniatis et al. supra.

(iv) Addition of dC tail

Double-stranded DNA from step(iii) was treated with nuclease S1 in 50 µl of a reaction solution (double-stranded DNA, 0.1M sodium acetate pH 4.5, 0.25M NaCl, 1.5 mM ZnSO₄, 60 units of S1 nuclease) at room temperature for 30 minutes, followed by deproteinization with phenol and DNA precipitation with ethanol. The DNA precipitate was treated with terminal transferase in 50 µl of a reaction solution (double-stranded DNA, 0.14M potassium cacodylate, 0.3M Tris (base) pH 7.6, 2 mM dithiothreitol, 1 mM CoCl₂, 0.15 mM dCTP, 30 units of terminal transferase) at 37° C. for 3 minutes to thereby cause extension of the double-stranded DNA by about 15 deoxycytidines at both the 3' ends. This series of reactions gave about 300 ng of a deoxycytidine chain-containing double-stranded DNA.

(v) Cleavage of *Escherichia coli* plasmid and addition of dG tail

Separately, 10 µg of *Escherichia coli* plasmid pBR322 DNA was treated with the restriction enzyme PstI in 50 µl of a reaction solution (10 µg of said DNA, 50 mM NaCl, 6 mM Tris·HCl pH 7.4, 6 mM MgCl₂, 6 mM 2-mercaptoethanol, 100 µg/ml bovine serum albumin, 20 units of PstI) at 37° C. for 3 hours to thereby cleave the one PstI recognition site occurring in the pBR322 DNA, followed by deproteinization with phenol. The cleaved plasmid pBR322 DNA was extended by about 17 deoxyguanines at both of its 3' ends by treating said DNA with terminal transferase in 50 μl of a reaction solution (10 μg of DNA, 0.14M potassium cacodylate, 0.3M Tris base pH 7.6, 2 mM dithiothreitol, 1 mM CoCl$_2$, 0.15 mM GTP and 30 units of terminal transferase) at 37° C. for 3 minutes.

(vi) Annealing of cDNA and transformation of *Escherichia coli*

DNA coding for IL-2 obtained in (iv) above (0.1 μg) and 0.5 μg of plasmid DNA from (v) above were annealed by heating in a solution containing 0.1M NaCl, 50 mM Tris·HCl pH 7.6 and 1 mM EDTA at 65° C. for 2 minutes and then at 45° C. for 2 hours followed by gradual cooling and the product was used for transformation of *Escherichia coli* MM294 in accordance with the method of Enea et al. [J. Mol. Biol., 96, 495 (1975)].

(vii) Isolation of cDNA-containing plasmid

In this way, about 20,000 tetracycline-resistant transformants were isolated. DNAs of each of them were fixed on a nitrocellulose filter. Based on the amino acid sequence of IL-2 reported by Taniguchi et al. [Nature, 302, 305 (1983)], the complementary oligonucleotides of base sequences (5'AAA CAT CTT CAG TGT3' and 5'ACA TTC ATG TGT GAA3') correponding to amino acids Nos. 74–78 (Lys-His-Leu-Gln-Cys) and amino acids Nos, 122–126 (Thr-Phe-Met-Cys-Glu), respectively, were chemically synthesized by the phosphotriester method [Crea, R. et al., Proc. Natl. Acad. Sci. USA, 75, 5765 (1978)].

These oligonucleotides were labeled with $^{32}$p at the 5' end by treatment with T4 polynucleotide kinase in 50 μl of a reaction solution (0.20 μg of oligonucleotide, 50 mM Tris·HCl pH 8.0, 10 mM MgCl$_2$, 10 mM 2-mercaptoethanol, 50 μCi of γ-$^{32}$p ATP, 3 units of T4 polynucleotide kinase) at 37° C. for 1 hour. These labeled oligonucleotides, as probes, were annealed with the above-mentioned DNAs fixed on nitrocellulose filter by the method of Lawn et al. [Nucleic Acids Res., 9, 6103 (1981)]. Four transformants reactive to the above two oligonucleotide probes were detected by autoradiography. Plasmid DNA was isolated from cells of each of these transformants by the Birnboim-Doly alkali method [Birnboim, H. C. & Doly, J., Nucleic Acids Res., 7, 1513 (1979)]. Then the insert in the plasmid DNA was cut out using the restriction enzyme PstI. From among the plasmids isolated, the one containing the longest insert encoding IL-2 was selected and named pILOT 135-8. The restriction enzyme map of this plasmid is shown in FIG. 1.

The primary structure (base sequence) of the cDNA inserted in this pILOT 135-8 was determined by the dideoxynucleotide method and the Maxam-Gilbert method. The primary structure thus determined is shown in FIG. 2. The peptide defined by this base sequence consists of 153 amino acids, starting with the synthesis start signal (Nos. 64–66 ATG). Of these, the 20 amino acids from the N-terminal are considered to constitute a signal peptide. The above primary structure has revealed that pILOT 135-8 has a base sequence coding for human IL-2 protein. This fact indicates that insertion of a gene coding for IL-2 obtained in (iv) above into an appropriate expression plasmid can lead to production of the IL-2 protein.

REFERENCE EXAMPLE 2

Figure 4:
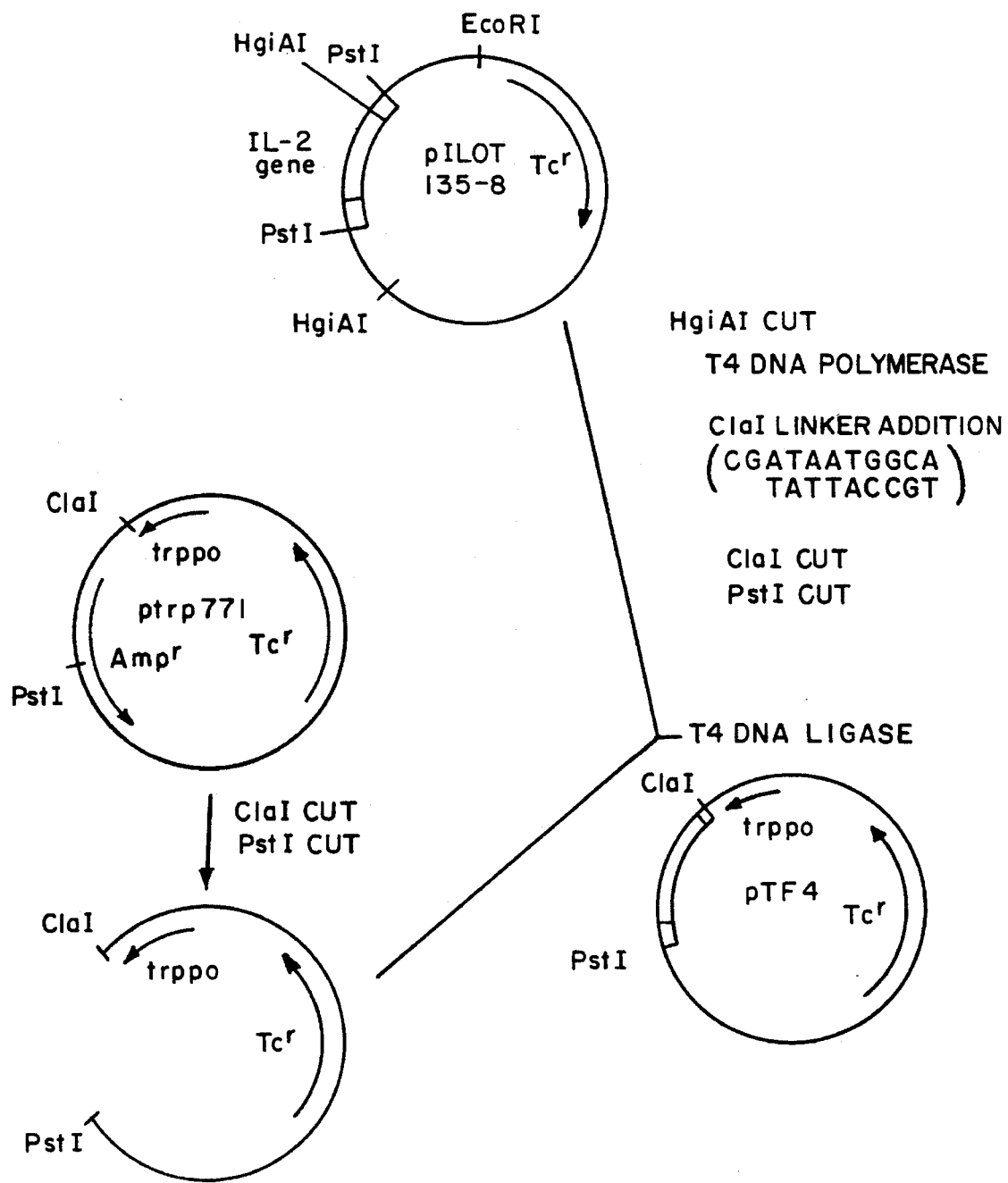
FIG. 4 shows the scheme of constructing the expression plasmid pTF4 as set forth in Reference Example 2.

The plasmid pILOT135-8 obtained in Reference Example 1 was cleaved with the restriction enzyme HgiAI. The thus-obtained 1294 bp DNA fragment containing an IL-2 gene was treated with T4 DNA polymerase, joined with the ClaI linker CGATA ATG GCA, which contained the codon GCA for alanine and the codon ATG for methionine, and the product was treated with ClaI and PstI, followed by insertion into ptrp771 at the ClaI-PstI site. The expression plasmid thus obtained was named pTF4 (FIG. 4).

REFERENCE EXAMPLE 3

*Escherichia coli* DH1 was transfomed with the plasmid pTF4 obtained in Reference Example 2 in accordance with the method of Cohen et al. [Proc. Natl. Acad. Sci. USA, 69, 2110 (1972)] to obtain a transformant (*Escherichia coli* DH1/pTF4 ) carrying said plasmid.

EXAMPLE 1

(i) *E. coli* DH1/pTF4 (obtained in Reference Example 3) was inoculated into 50 ml of a liquid medium (pH 7.0) containing 1% Bacto tryptone (Difco Laboratories, USA), 0.5% Bacto yeast extract (Difco Laboratories, USA), 0.5% sodium chloride and 7 μg/ml tetracycline and placed in a 250-ml erlenmeyer flask. After incubation at 37° C. overnight on a swing rotor, the culture medium was transferred to a 5-liter jar fermenter containing 2.5 liters of M9 medium containing 0.5% casamino acids, 0.5% glucose and 7 μg/ml tetracycline. Incubation was then conducted with aeration and stirring at 37° C. for 4 hours and, after addition of 3-β-indolylacrylic acid (25 μg/ml), for an additional 4 hours. Cells were harvested from the thus-obtained 2.5-liter culture broth by centrifugation, frozen at −80° C. and stored.

(ii) The freeze-stored cells (12.1 g) obtained in Example 1(i) were suspended in 100 ml of an extractant (pH 7.0) containing 7M guanidine hydrochloride and 0.1M Tris·HCl, the suspension was stirred at 4° C. for 1 hour and the lysate was centrifuged at 28,000×g for 20 minutes to obtain 93 mi of a supernatant.

(iii) Separately, various procedures were conducted to extract IL-2 from the transformant *E. coli* DH1/pTF4 cells obtained by the method of Example 1 (i) to compare the respective extraction efficiencies.

In the lysozyme-EDTA method, 2 g of *E. coli* DH1/pTF4 cells obtained in Example 1(i) were mixed with 16 ml of solution (pH7.0) containing 0.1M Tris-HCl, 10 mM EDTA and 250 mg/l lysozyme, the mixture was stirred at 4° C. for 1 hour and subseqently at 37° C. for 5 minutes and the lysate was centrifuged at 28,000×g for 20 minutes.

In the sonication method, 2 g of the cells from Example 1(i) were suspended in 16 ml of the solution (pH7.0) containing 0.1M Tris-HCl, the suspension was subjected to sonication at 0° C. for 5 minutes and the lysate was centrifuged at 28,000×g for 20 minutes.

In the guanidine-HCl method, 2 g of the cells from Example 1(i) were mixed with 16 ml of the solutions (pH7.0) containing 0.1M Tris-HCl and 2M, 4M or 7M guanidine-HCl, the mixtures were stirred at 4° C. for 1 hour and the lysates were centrifuged at 28,000×g for 20 minutes. The supernatant fluids thus obtained were used for the measurements of protein concentration and IL-2 activity.

The results are summarized in Table 2.

TABLE 2

Extraction of IL-2

| Extraction procedure | Protein concentration (mg/ml) | IL-2 activity in the extract (U/ml) | Relative ratio (%) |
|---|---|---|---|
| Lysozyme-EDTA | 5.40 | 3.3 | 0.02 |
| Sonication | 6.54 | 2.2 | 0.01 |
| 2M Gu.HCl | 2.60 | 46 | 0.2 |
| 4M Gu.HCl | 4.12 | 144 | 0.8 |
| 7M Gu.HCl | 7.22 | 19100 | 100 |

Gu.HCl: guanidine hydrochloride (iv) The supernatant fluid obtained in Example 1(ii) was dialyzed against 0.01M Tris·HCl buffer (pH 8.5) and then centrifuged at 19,000×g for 10 minutes to give 94 ml of a dialyzed supernatant fluid. This was applied to a DE 52 (DEAE-cellulose, Whatman, Great Britain) column (50 ml in volume) equilibrated with 0.01M Tris·HCl buffer (pH 8.5) for protein adsorption. Proteins were eluted with a linear NaCl concentration gradient (0–0.15M NaCl, 1 liter). The fractions with IL-2 activity (53 ml) were concentrated to 4.8 ml using a YM-5 membrane (Amicon, USA) and subjected to gel filtration using a Sephacryl S-200 (Pharmacia, Sweden) column (500 ml in volume) equibrated with 0.1M Tris·HCl (pH 8.0)-1M NaCl buffer. The active fractions (28 ml) thus obtained were concentrated to 2.5 ml using a YM-5 membrane. The concentrate was applied to an Ultrapore RPSC (Altex, USA) column for adsoprtion, and high performance liquid chromatography was performed using a trifluoroacetic acid-acetonitrile system as the mobile phase.

The conditions used: column, Ultrapore RPSC (4.6×75 mm); column temperature, 30° C.; solvent A, 0.1% trifluoroacetic acid-99.9% water; solvent B, 0.1% trifluoroacetic acid- 99.9% acetonitrile; elution program, minute 0 (68% A+32% B)–minute 25 (55% A+45% B)–minute 35 (45% A+55% B)–minute 45 (30% A+70% B)–minute 48 (100% B); elution rate, 0.8 ml/min; detection wave length, 230 nm. An active fraction was collected at a retention time of about 39 minutes. Thus was obtained 10 ml of a solution containing 0.53 mg of non-glycosylated human IL-2 protein [specific activity, 30,000 U/mg; activity recovery from the starting material, 30.6%; purity of protein, 99% (determined by densitometry on an SDS-polyacrylamide gel electrophoretogram)].

Lyophilization of the above solution gave a white powder. The powder had a specific activity of 26,000 U/mg.

Figure 5:
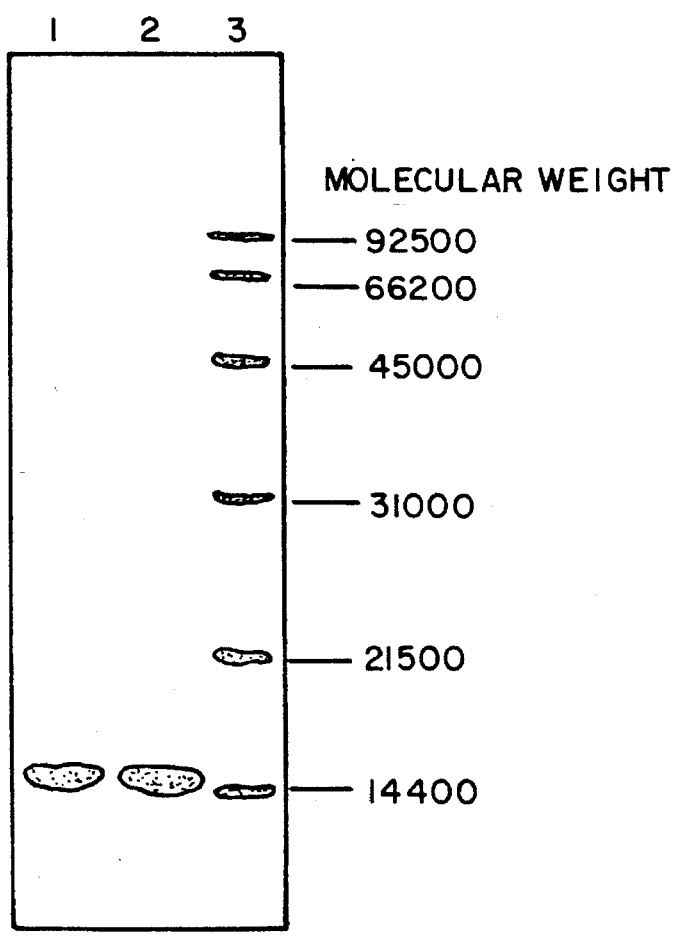
FIG. 5 shows the results of the SDS-polyacrylamide slab gel electrophoresis performed in Example 1(V) (1) and (2)

(V) Human IL-2 protein obtained in Example 1 (iv) was examined for the following properties:

(1) Homogeneity:

Staining with Coomassie Brilliant Blue following SDS-polyacrylamide gel electrophoresis according to Laemmli et al. [Nature, 227, 680 (1970)] revealed only a single band of said human IL-2 protein (cf. FIG. 5). The location of the band remained unchanged under reducing conditions as well as under non-reducing conditions.

(2) Molecular weight:

The molecular weight of said human IL-2 protein was calculated to be about 15,000 daltons based on the result of SDS-polyacrylamide gel electrophoresis (cf. FIG. 5).

(3) Amino acid composition:

A 20-μg portion of said human IL-2 protein was placed in a glass test tube for hydrolysis, constant boiling hydrochloric acid containing 4% thioglycolic acid was added, the tube was then sealed in vacuo and hydrolysis was performed at 110° C. for 24, 48 or 72 hours. After hydrolysis, the tube was opened, the hydrochloric acid was removed under reduced pressure, and the residue was dissolved in 0.02N hydrochloric acid and subjected to amino acid analysis using a Hitachi model 835 amino acid analyzer. For determination of cystine and cysteine, said human IL-2 protein was oxidized with performic acid by the method of Hirs [Methods in Enzymol., 11, 197 (1967)] followed by hydrolysis in constant boiling hydrochloric acid under reduced pressure for 24 hours. The hydrolyzate was subjected to cysteic acid determination using an amino acid analyzer. The results obtained by the above amino acid analyses are shown in Table 3. The values are each the mean of three values respectively obtained after 24, 48 and 72 hours of hydrolysis except for the values for serine and threonine which were determined by extrapolation to zero time of hydrolysis.

TABLE 3

| Amino acid | Mole % |
|---|---|
| Asp/Asn | 8.8 |
| Thr | 9.3 |
| Ser | 5.7 |
| Glu/Gln | 13.7 |
| Pro | 3.4 |
| Gly | 1.7 |
| Ala | 3.8 |
| ½ Cys | 2.3 |
| Val | 3.1 |
| Met | 3.7 |
| Ile | 6.3 |
| Leu | 16.3 |
| Tyr | 2.3 |
| Phe | 4.5 |
| Lys | 8.3 |
| His | 2.5 |
| Arg | 3.1 |
| Trp | 1.1 |

(4) N-Terminal amino acid sequence:

A 34-μg portion of said human Il-2 protein was analyzed for the N-terminal amino acid sequence by applying the automatic Edman degradation method using a gas-phase protein sequenator (model 470A, Applied Biosystems, USA). Phenylthiohydantoin-amino acids (PTH-amino acids) were identified by high performance liquid chromatography using a Micropak-SP column (Varian, USA). The PTH-amino acid or acids detected in each step are shown in Table 4.

TABLE 4

| Step | PTH-amino acid detected |
|---|---|
| 1 | Ala |
|   | Met |
| 2 | Pro |
|   | Ala |
| 3 | Thr |
|   | Pro |
| 4 | Ser |
|   | Thr |
| 5 | Ser |
| 6 | Ser |
| 7 | Thr |
| 8 | Lys |
| 9 | Lys |
| 10 | Thr |
| 11 | Gln |
| 12 | Leu |
| 13 | Gln |
| 14 | Leu |

TABLE 4-continued

| Step | PTH-amino acid detected |
| --- | --- |
| 15 | Glu |
| 16 | Y* |
| 17 | Leu |
| 18 | Leu |
| 19 | Leu |
| 20 | Asp |

*Not yet identified.

(5) C-Terminal amino acid:

A 33-μg portion of said human IL-2 protein was placed in a glass test tube for hydrazine degradation, 0.05 ml of anhydrous hydrazine was added and the tube was sealed in vacuo and heated at 100° C. for 6 hours. The hydrazine degradation product obtained was lyophilized and dissolved in distilled water. Benzaldehyde was added to the solution, the mixture was stirred at room temperature for 1 hour and then centrifuged. The aqueous layer thus obtained was lyophilized and subjected to amino acid analysis using a Hitachi model 835 amino acid analyzer. Threonine alone was detected.

(6) Tryptic peptide mapping

Figure 6:
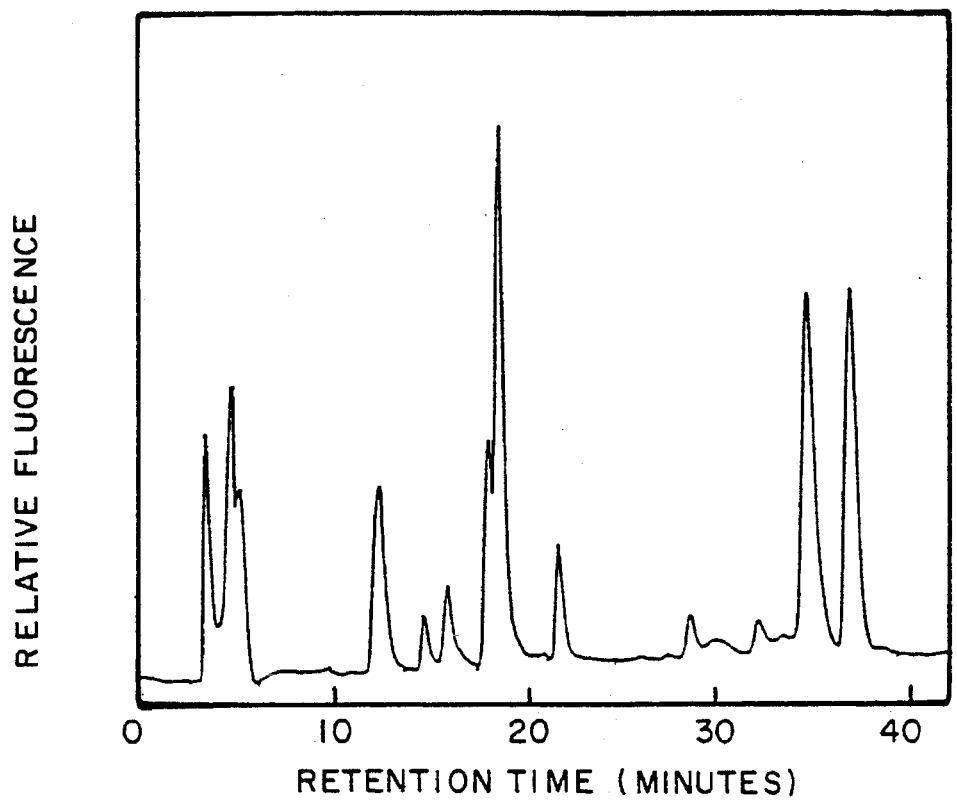
FIG. 6 shows the trypsin digestion peptide map mentioned in Example 1 (V) (6)

A 15-μg portion of said human IL-2 protein was digested with 0.4 μg of trypsin (Washington, USA) in 120 μl of 0.02M sodium hydrogen carbonate at 37° C. for 18 hours. Then, 5 μl of 2-mercaptoethanol was added and the reaction was continued at 37° C. for an additional 2 hours. Thereafter, the reaction was terminated by addition of 75 μl of 1% trifluoroacetic acid. High performance liquid chromatography of the reaction mixture, which was performed under the conditions given below, gave an elution pattern shown in FIG. 6.

Column: Ultrasphere-Octyl (5 μm, 4.6×250 mm; Altex, USA);

Column temperature: 30° C.;

Mobile phase:

Solvent A, 0.02% trifluoroacetic acid-99.98% water;

Solvent B, 0.02% trifuloroacetic acid-99.98% acetonitrile;

Minute 0 (95% solvent A+5% solvent B)-minute 40 (30% solvent A+70% solvent B);

Flow rate: 1.0 ml/minute;

Detection: Fluorescence method [Analytical Biochem., 67, 438 (1975)] using fluorescamine (Roche, USA).

(7) Activity against IL-2-dependent cell lines

Figure 7:
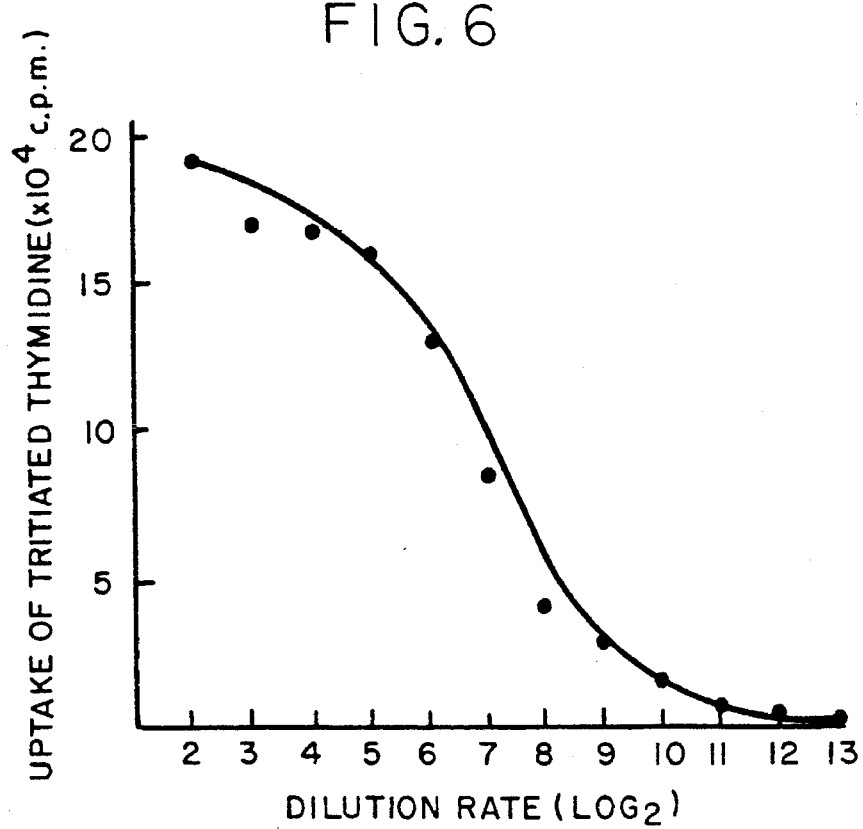
FIG. 7 and FIG. 8 show the effects of human IL-2 protein according to the invention on the uptake of tritiated thymidine by the NKC3 cell line and human cell line, respectively, as revealed in Example 1(V) (7).
Figure 8:
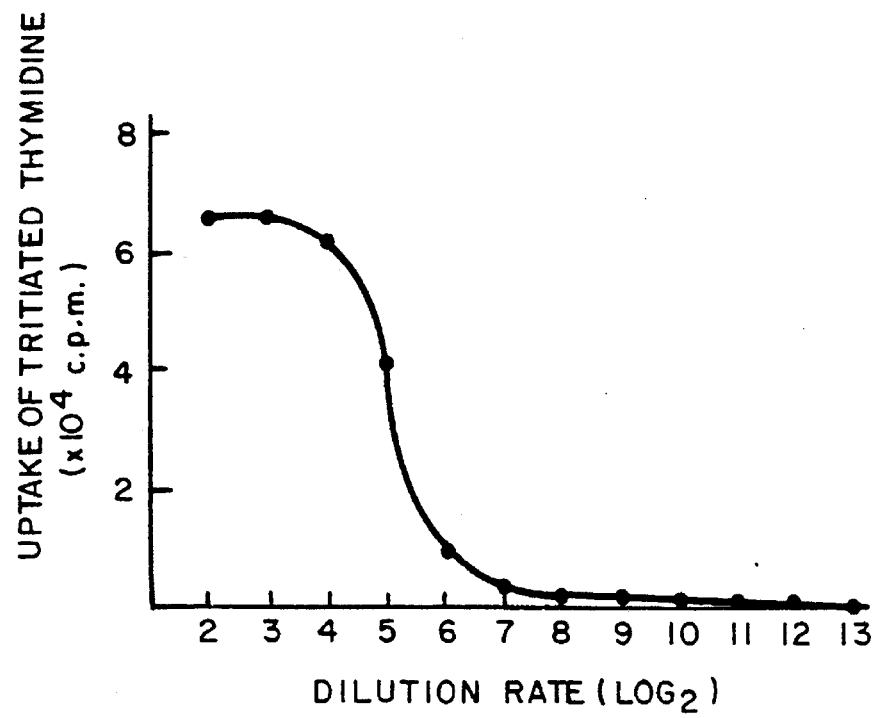

Assay of non-glycosylated human IL-2 protein according to the invention in accordance with the method described in Biochem. Biophys. Res. Commun., 109, 363 (1982) revealed that said IL-2 protein had an activity that promoted tritiated thymidine uptake in an IL-2-dependent mouse cell line (NKC3; cf. FIG. 7) as well as in an IL-2-dependent human cell line (cf. FIG. 8).

Figure 9:
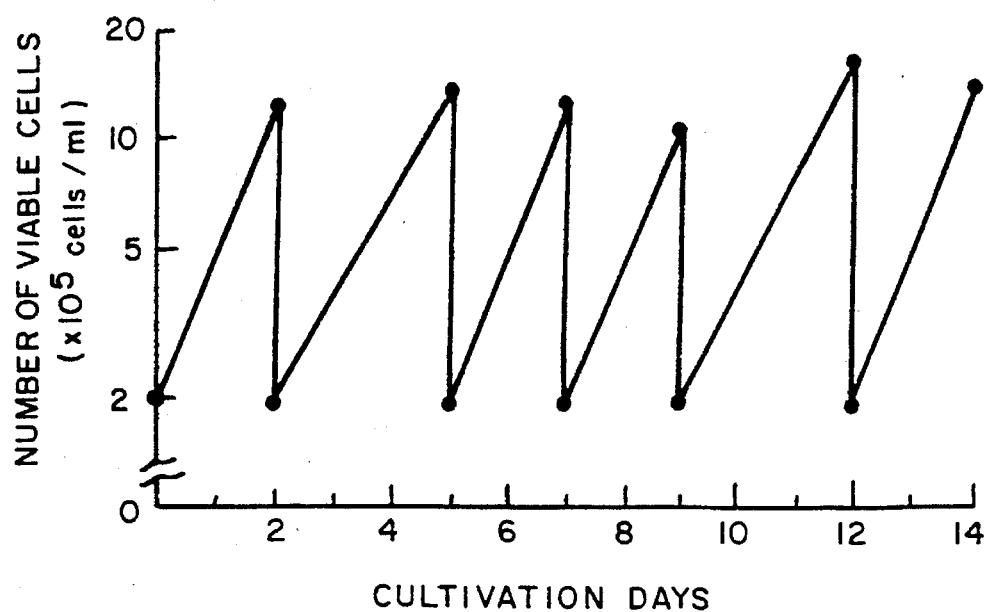
FIG. 9 shows the results of the long-period subculturing of the NKC3 cell line conducted in Example 1(V) (7).

Furthermore, said IL-2 protein was dissolved in 20% FCS-added RPMI-1640 medium to a concentration of 0.5 U/ml, and 2×10$^5$ cells/ml of the NKC3 cell line were suspended in the medium. Subculturing was continued on a Linbro Multi dish (Flow, USA) at 37° C. in the presence of 5% $CO_2$ while repeating viable cell counting and resuspending the culture in a new fresh medium at 2- or 3-day intervals. As a result, said IL-2 protein was found to have an activity to maintain the growth of the NKC3 cell line for a long period of time, as illustrated in FIG. 9.

EXAMPLE 2

(Preparation for injection)

The non-glycosylated human IL-2 protein-containing solution obtained in Example 1 (iv) is applied to a CM Toyopearl (Toyo Soda, Japan) column equilibrated with 0.025M ammonium acetate buffer (pH 5.0) under aseptic conditions for adsorption, followed by elution with the above buffer containing 0.15M NaCl. The eluate is diluted by addition of an appropriate amount of 0.15M NaCl, then HSA is added to a concentration of 0.5%, and the mixture is filtered through a membrane filter (0.22 μm in pore diameter). The filtrate is distributed aseptically in 1-ml portions into vials, followed by lyophilization. The human IL-2 preparation for injection in each vial is dissolved in 1 ml of distilled water for injection prior to use.

REFERENCE EXAMPLE 4

The plasmid pILOT 135-8 obtained in Reference Example 1 was cleaved with the restriction enzyme HgiAI. The thus-obtained 1294 bp DNA fragment was treated with T4 DNA polymerase to have flat ends and was connected with EcoRI linker dTGCCATGAATTCATGGCA by using T4 DNA ligase. The thus-obtained DNA was digested with EcoRI to obtain a DNA fragment which additionally had translational start codon ATG and human IL-2 gene.

Figure 10:
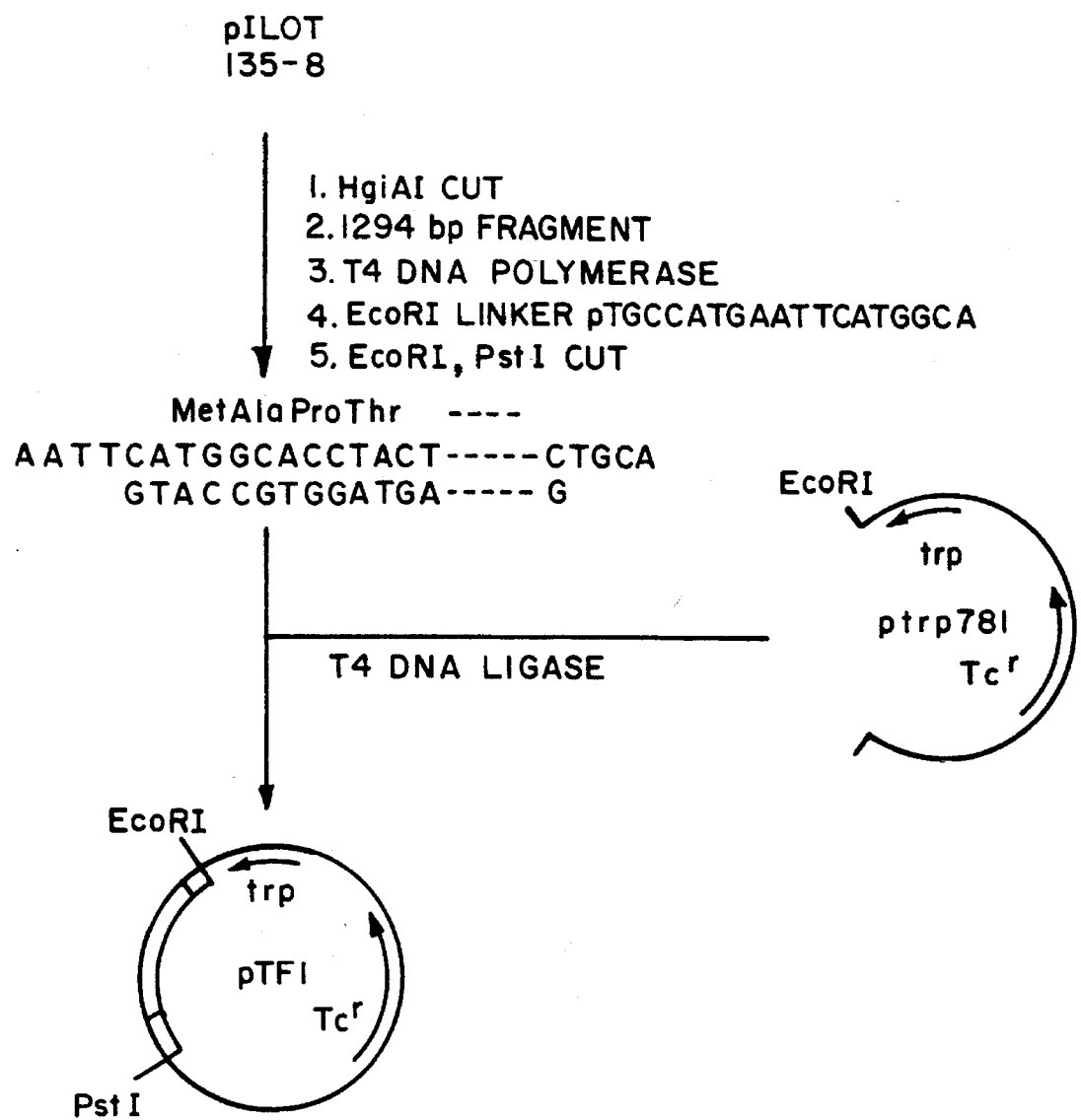
FIG. 10 and FIG. 11 show schemes of constructing the expression plasmids pTF 1 and pTB285 as set forth in Reference Example 4.

This DNA fragment was inserted by using T4 DNA ligase into ptrp 781 [Nucleic Acids Research, 11, 3077 (1983)] which had been digested at the EcoRI-PstI site. The thus obtained expression plasmid pTF 1 had a translational start codon and a human IL-2 gene downstream from the trp promoter (FIG. 10).

Figure 11:
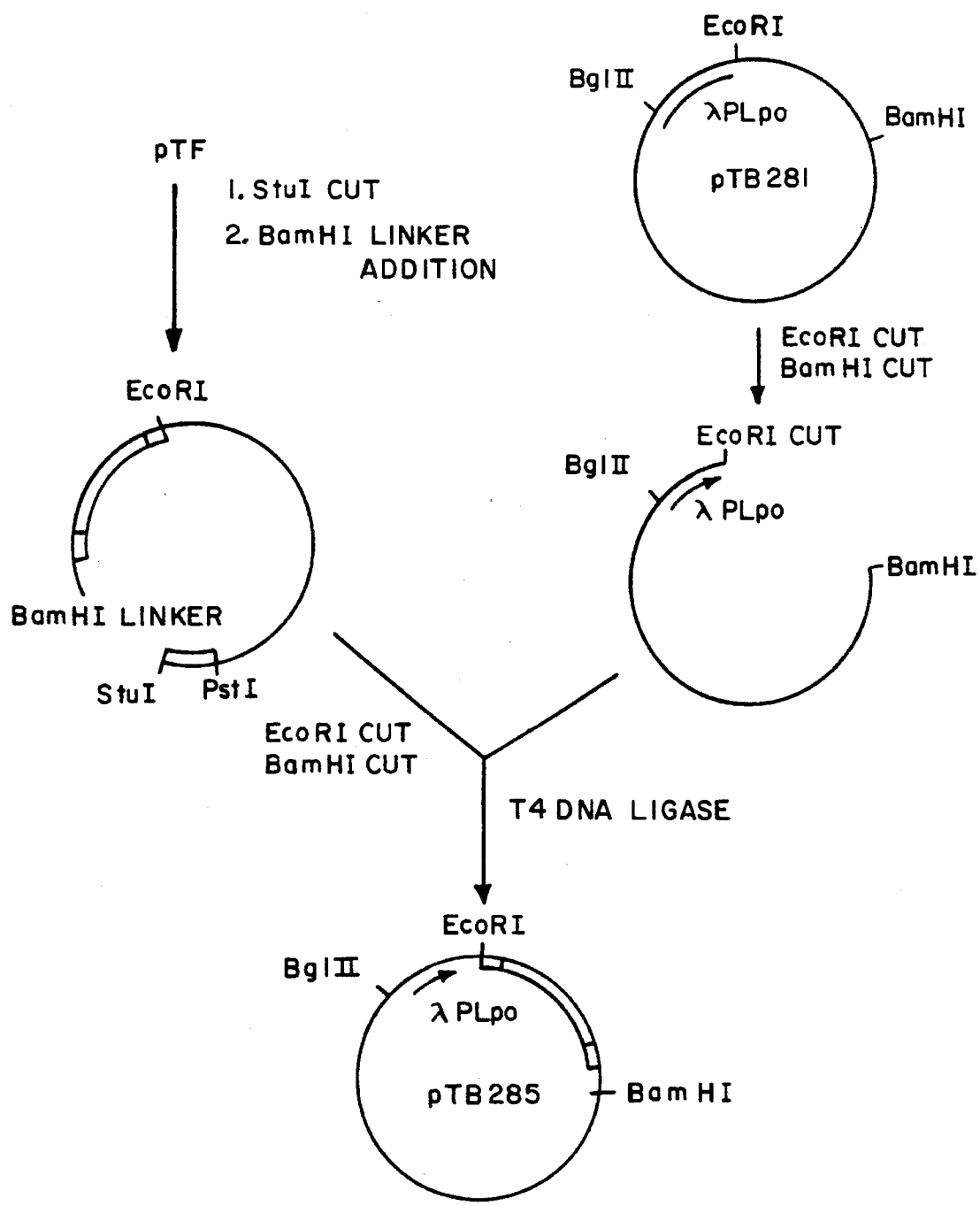

The plasmid pTF 1 was cleaved with the restriction enzyme StuI and joined with the BamHI linker. This plasmid DNA was treated with the restriction enzymes BamHI and EcoRI, followed by insertion into pTB 281, which has the λPL promoter at the EcoRI-BamHI site. The expression plasmid thus obtained was named pTB 285 (FIG. 11).

REFERENCE EXAMPLE 5

*Escherichia coli* N4830 was transformed with the plasmid pTB285 obtained in Reference Example 4 in accordance with the method of Cohen et al. [vide supra] to obtain a transformant (*Escherichia coli* N4830/pTB285) carrying said plasmid.

EXAMPLE 3

*E. coli* N4830/pTB285 obtained in Reference Example 5 was inoculated into 50 ml of a liquid medium (pH 7.0) containing 1% Bacto tryptone (Difco Laboratories, USA), 0.5% Bacto yeast extract (Difco Laboratories, USA), 0.5% sodium chloride and 7 μg/ml tetracycline and placed in a 250-ml erlenmeyer flask. After incubation at 35° C. overnight on a swing rotor, the culture medium was transferred to a 5-liter jar fermenter containing 2.5 liters of M9 medium containing 0.5% casamino acids, 0.5% glucose and 7 μg/ml tetracycline. Incubation was then conducted with aeration and stirring at 35° C. for 4 hours and 42° C. for an additional 3 hours. Cells were harvested from the thus-obtained 2.5-liter culture broth by centrifugation, frozen at −80° C. and stored.

By the extraction and purification of said cells according to Example 1, highly purified human IL-2 protein having the same properties as that in Example 1 (V) was obtained from the *E. coli* N4830/pTB285 cells mentioned above.

The following references, which are referred to for their disclosures at various points in this application, are incorporated herein by reference.

Science, 193, 1007–1008 (1976)
Immunological Reviews, 51, 257–278 (1980)
The Journal of Immunology, 123, 2928–2929 (1979)
Nature, 268, 154–156 (1977)
The Journal of Immunology, 130, 981–987 (1983)
ibid., 125, 1904–1909 (1980)
ibid., 130, 1784–1789 (1983)
ibid., 130, 1970–1973 (1983)
European Journal of Immunology, 10, 719–722 (1980)
Nature, 284, 278–280 (1980)
Nature, 302, 305–310 (1983)
Nucleic Acids Research, 11, 4307–4323 (1983)
Biochemical and Biophysical Research Communication, 109, 363–369 (1982)
Cell, 8, 163–182 (1976)
Nucleic Acids Research 9, 2251–2266 (1981)
Methods in Enzymology, 68, 41–50 (1979)
Proc. Natl. Acad. Sci. USA, 72, 3961–3965 (1975)
Method in Enzymology, 68, 220–242 (1979)
Proc. Natl. Acad. Sci. USA, 74, 560–564 (1977)
Nucleic Acids Research, 9, 309–321 (1981)
Proc. Natl. Acad. Sci. USA, 73, 4174–4178 (1976)
Nature, 217, 1110–1114 (1968)
Cell, 25, 713–719 (1981)
Proc. Natl. Acad. Sci. USA, 69, 2110–2114 (1972)
J. Experiments in Molecular Genetics, pages 431–433 (Cold spring Harbor Laboratory, New York, 1972)
Journal of Immunology, 130, 988–992 (1983)
The Journal of Immunology, 120, 2027–2032 (1978)
Haemostasis, 7, 183 (1978)
J. Molecular Biology, 96, 495–509 (1975)
Proc. Natl. Acad. Sci. USA, 75, 5765–5769 (1978)
Nucleic Acids Research, 9, 6103–6114 (1981)
ibid., 7, 1513–1523 (1979)
Methods in Enzymology, 11, 197–199 (1967)
Analytical Biochem., 67, 438–445 (1975)
Nucleic Acids Research, 11, 3077–3085 (1983)

What is claimed is:

1. A substantially pure non-glycosylated human interleukin-2 protein having a specific activity of not less than $10^4$ U/mg, which reacts negatively in the limulus lysate test.

2. A protein according to claim 1, which has a amino acid sequence of the formula:

```
X-Ala Pro Thr Ser Ser Ser Thr Lys Lys Thr Gln Leu Gln
Leu Glu His Leu Leu Leu Asp Leu Gln Met Ile Leu Asn
Gly Ile Asn Asn Tyr Lys Asn Pro Lys Leu Thr Arg Met
Leu Thr Phe Lys Phe Tyr Met Pro Lys Lys Ala Thr Glu
Leu Lys His Leu Gln Cys Leu Glu Glu Glu Leu Lys Pro
Leu Glu Glu Val Leu Asn Leu Ala Gln Ser Lys Asn Phe
His Leu Arg Pro Arg Asp Leu Ile Ser Asn Ile Asn Val
Ile Val Leu Glu Leu Lys Gly Ser Glu Thr Thr Phe Met
```

-continued
```
Cys Glu Tyr Ala Asp Glu Thr Ala Thr Ile Val Glu Phe
Leu Asn Arg Trp Ile Thr Phe Cys Gln Ser Ile Ile Ser
Thr Leu Thr
``` wherein X is Met or hydrogen.

3. A protein according to claim 1, which is in a freeze dried lyophilized form.

4. A pharmaceutical composition which comprises a substantially pure non-glycosylated human interleukin-2 protein having a specific activity of not less than $10^4$ U/mg, which reacts negatively in the limulus lysate test, and a pharmaceutically acceptable carrier, vehicle or diluent therefor.

5. A composition according to claim 4, which is an injectable preparation.

6. A method of producing a pharmaceutical composition containing a substantially pure non-glycosylated human interleukin-2 protein having a specific activity of not less than $10^4$ U/mg, which comprises admixing said protein with a pharmaceutically acceptable carrier, vehicle or diluent therefor.

7. A substantially pure human Interleukin-2 protein which is purified from a microbial transformant using reverse phase HPLC, wherein the purified protein exhibits a specific activity of at least $1 \times 10^4$ U/mg, which reacts negatively in the limulus lysate test.

8. The human Interleukin-2 protein of claim 7 which has a purity of about 99% as determined by SDS-PAGE.

9. The human Interleukin-2 protein of claim 7 which displays a single band on SDS-PAGE analysis under both reducing and non-reducing conditions.

10. The non-glycosylated human interleukin-2 protein of claim 1 having a purity of about 99% as determined by SDS-PAGE.

11. The pharmaceutical composition of claim 4, wherein the non-glycosylated human interleukin-2 protein has a purity of about 99% as determined by SDS-PAGE.

12. A purified recombinant human Interleukin-2 (IL-2) composition wherein the IL-2 is unglycosylated and active, having an IL-2 content of at least about 95% as determined by reducing SDS-PAGE analysis, and reacts negatively in the limulus lysate test and is thus low in protein impurity and pyrogens.

13. The purified recombinant IL-2 composition of claim 12, wherein the IL-2 content is greater than about 99% as determined by reducing SDS-PAGE.

14. The purified recombinant human IL-2 composition of claim 12, wherein the composition is purified using a purification process comprising hydrophobic column chromatography from a human interleukin-2-containing liquid obtained by a method comprising growing a transformant carrying a DNA segment having a base sequence coding for human interleukin-2 to cause production and accumulation of human interleukin-2 in the culture broth.

15. The purified recombinant human IL-2 composition of claim 14, wherein the hydrophobic column chromatography is a high performance liquid chromatography using a reversed phase column.

* * * * *